United States Patent [19]

Kelley et al.

[11] 4,227,190
[45] Oct. 7, 1980

[54] WATER ALARM FOR MONITORING FLOOR MOISTURE

[76] Inventors: Jerry K. Kelley, 3121 N. Nottingham, Chicago, Ill. 60634; Eugene V. Mateja, 7917 W. Courtland, Norridge, Ill. 60656

[21] Appl. No.: 14,976

[22] Filed: Feb. 26, 1979

[51] Int. Cl.² .............................................. G08B 21/00
[52] U.S. Cl. .................. 340/604; 73/304 R; 340/620
[58] Field of Search ............... 340/555, 602, 603, 604, 340/605, 612, 616, 618, 620, 623, 624, 631; 324/65 R; 73/304 R, 313; 200/84 R, 84 A, 84 B

[56] References Cited

U.S. PATENT DOCUMENTS

| | | | |
|---|---|---|---|
| 1,222,183 | 4/1917 | Cohen | 200/84 R |
| 3,310,795 | 3/1967 | David | 340/624 |
| 3,399,399 | 8/1968 | Apfelbaum | 340/620 X |
| 3,562,731 | 2/1971 | Hsu | 340/604 |
| 3,636,542 | 1/1972 | Apple | 340/555 |
| 3,732,556 | 5/1973 | Caprillo et al. | 340/620 X |
| 3,758,855 | 9/1973 | Meyer | 324/65 R |
| 3,889,247 | 6/1975 | Voll | 73/313 X |
| 3,942,167 | 3/1976 | McClintock | 340/620 |
| 4,011,553 | 3/1977 | Delgado Barri | 340/605 |
| 4,080,593 | 3/1978 | Gernandt et al. | 340/631 X |
| 4,126,857 | 11/1978 | Lancia et al. | 340/620 |

Primary Examiner—John W. Caldwell, Sr.
Assistant Examiner—Daniel Myer
Attorney, Agent, or Firm—Kinzer, Plyer, Dorn & McEachran

[57] ABSTRACT

A self-contained water alarm for monitoring floor moisture comprising a plurality of pairs of sensor electrodes mounted at spaced locations on the bottom of a donut-shaped housing that can be fitted over a standpipe, the sensor electrode pairs being incorporated in feet that support the housing on a floor; the housing contains a horn or other audible alarm device, a battery, and an alarm circuit including an SCR having its main anode-cathode disclosure path connected in series with the horn and the battery and in parallel with a manual test-reset switch, and having its gate electrode connected to one sensor electrode in each pair, the other sensor electrode in each pair being connected to the battery. An auxiliary pair of sensor electrodes are connected in the circuit, in parallel with the housing-mounted sensor electrode pairs, to permit simultaneous monitoring of floor moisture and of the water level in a sump or standpipe. Provision is made for connecting a remote alarm to the device.

4 Claims, 7 Drawing Figures

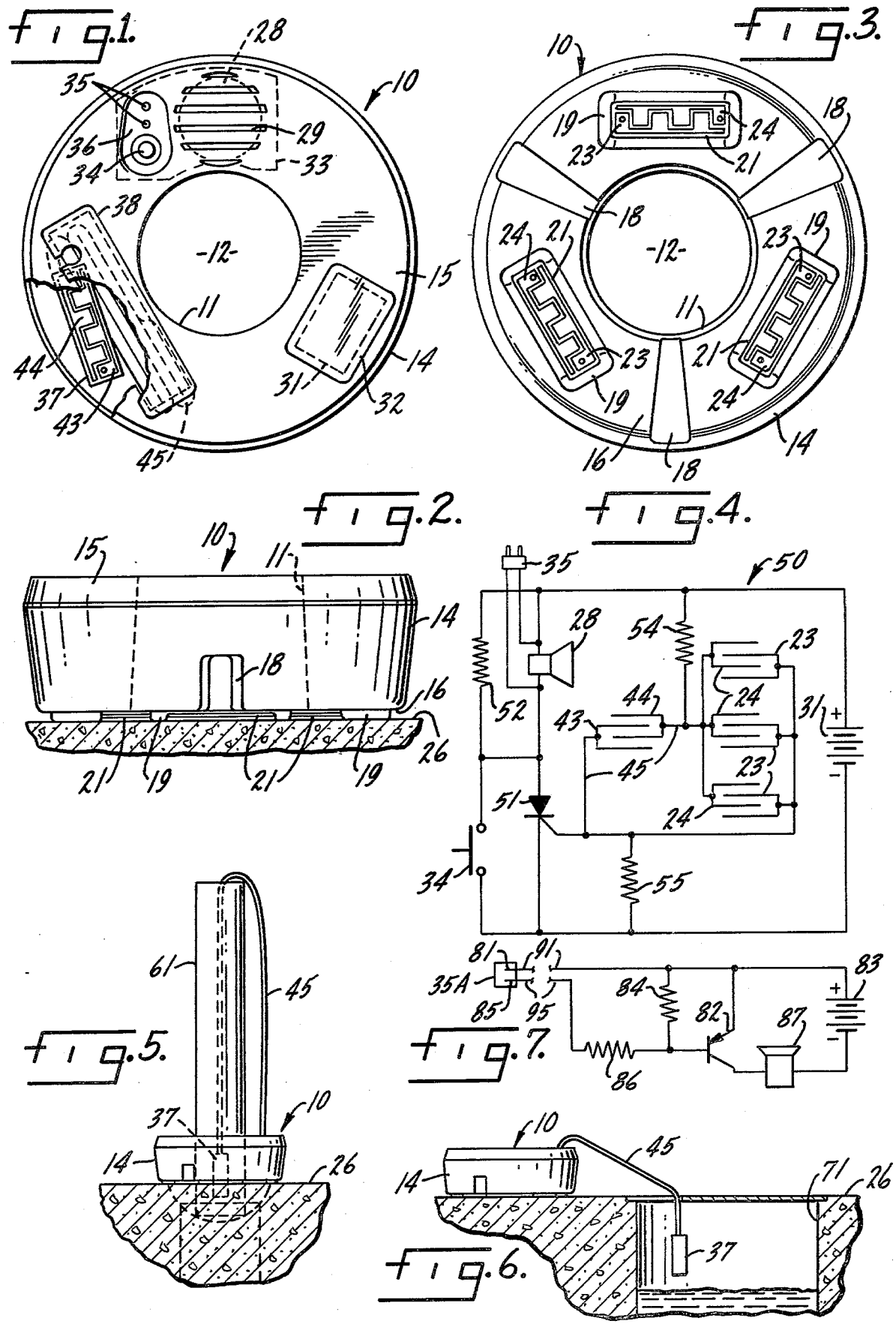

WATER ALARM FOR MONITORING FLOOR MOISTURE

BACKGROUND OF THE INVENTION

A continuing, widely prevalent problem for the owners and occupants of housing having a basement or other floor at or below grade is presented by the accumulation of water on the floor, leading to damage to furniture and other property and occasionally to structural damage to the building. A similar problem can be presented above grade, particularly in laundry rooms and in other locations in which a plumbing failure may lead to flooding of a floor. Devices for monitoring floor moisture conditions, setting off an audible alarm or visual alarm in the presence of water on the floor, have been proposed. However, such water alarm devices have not been generally accepted for a variety of reasons.

Many of the previously proposed floor water monitoring alarms are unduly complex and expensive for general housing use. Some devices of this nature have been constructed for energization from the electrical power lines in the house, a most undesirable arrangement because power line failures often occur during the kind of storm that is most likely to produce water problems in basements and on floors located at grade.

A particular problem of previously known floor monitoring water alarms is the lack of any convenient means for testing the alarm in the face of impending storm conditions. That is, when a heavy rainstorm is due, the home owner or occupant in a dwelling likely to incur floor water problems needs the reassurance of a convenient and accurate test to determine whether a floor monitoring water alarm is in good operating condition.

Another difficulty associated with previously known floor water alarms is a lack of versatility. The alarm, to be truly effective, should be readily adaptable to simultaneous monitoring of the water level in a sump or a standpipe associated with the floor. By the same token, the sensitivity of the alarm should be established at a level that will not give a false warning under ordinary conditions of dampness in a basement location.

SUMMARY OF THE INVENTION

It is a principal object of the present invention, therefore, to provide a new and improved self-contained water alarm for monitoring floor moisture that is simple and inexpensive in construction yet highly reliable in operation.

A further object of the invention is to provide a new and improved self-contained water alarm for monitoring floor moisture that can be readily and instantaneously tested at any given time to make certain that the alarm is operable.

Another object of the invention is to provide a novel, self-contained water alarm for monitoring floor moisture of improved versatility, capable of simultaneously monitoring the water level in a sump or standpipe related to the floor being monitored, and having a sensitivity level that precludes false alarms under conditions of dampness that do not constitute a threat.

Accordingly, the invention relates to a self-contained water alarm for monitoring floor moisture, comprising a housing having a plurality of support feet for supporting the housing on a floor with the bottom of the housing in close spaced relation to the floor, a plurality of pairs of printed circuit sensor electrodes, each electrode pair being mounted on the outside of the bottom of the housing in a position protected from floor contact by the support feet, the sensor electrodes of each pair being in closely spaced relation to each other immediately above the floor on which the housing is supported, the resistance between the sensor electrodes being very high when the floor is dry and much lower when the floor is covered with water to a depth sufficient to contact the electrodes, an electrically actuated audible alarm device, mounted within the housing, and battery mounting means for mounting a battery within the housing. An alarm circuit is mounted within the housing and interconnects the alarm device, the battery, and the sensor electrodes; the alarm circuit comprises a solid-state switching device, connected to each pair of sensor electrodes and actuatable from a normal nonconductive condition to a sustained conductive condition in response to a low resistance condition between any pair of the sensor electrodes, the switching device having a main discharge path connected in series with the alarm device and the battery, and an auxiliary pair of sensor electrodes mounted on a small pad and electrically connected in parallel with the housing-mounted pairs of sensor electrodes through an elongated extension cord to permit simultaneous monitoring of floor moisture and of the water level in a sump or in a standpipe, the housing including a storage compartment for storing the auxiliary electrode pad and cord when not in use.

BRIEF DESCRIPTION OF THE DRAWINGS

FIG. 1 is a plan view of a self-contained water alarm for monitoring floor moisture, constructed in accordance with a preferred embodiment of the present invention;

FIG. 2 is an elevation view of the water alarm of FIG. 1;

FIG. 3 is a bottom view of the water alarm of FIGS. 1 and 2;

FIG. 4 is a schematic diagram of the electrical circuit for the water alarm of FIGS. 1-3;

FIG. 5 illustrates the water alarm of FIGS. 1-4 in use in conjunction with a standpipe;

FIG. 6 illustrates the water alarm of FIGS. 1-4 in use in connection with a sump; and FIG. 7 is a schematic circuit diagram of a remote alarm used with the alarm of FIGS. 1-4.

DESCRIPTION OF THE PREFERRED EMBODIMENT

FIGS. 1-3 illustrate the mechanical construction for a self-contained floor moisture water alarm 10 constructed in accordance with a preferred embodiment of the present invention. Alarm 10 comprises a housing of annular configuration having an inside wall 11 encompassing a central aperture 12 and an outside wall 14. The housing of alarm 10 further includes a cover 15 and a base or bottom wall 16. Three partitions 18 divide the interior of the alarm housing into three interconnected compartments.

Three sensor pads 21 are mounted on the base wall 16, each located within a rectangular rim 19 constituting a support foot for the alarm (FIGS. 2, 3). Feet 19 are molded integrally with bottom wall 16. Each of the pads 21 has a pair of sensor electrodes 23 and 24 mounted on its bottom surface; sensor electrodes are positioned just above a floor 26 when alarm 10 is in use.

Sensor electrodes 23 and 24 are thin, electrically conductive elements, preferably of a material that will withstand some abrasion if alarm 10 is moved around on the floor surface 26. Rims 19 should allow water on the floor to have free access to pads 21 and electrodes 23,24; the electrodes are preferably spaced about 1/16 inch or less above the floor. Pads 21 can be employed as the feet for alarm 10, eliminating the rims 19, but that arrangement increases the possibility of excessive wear on the sensor electrodes and also increases the possibility of a false alarm due to mere condensation on the floor surface.

A horn or other electrically actuated alarm device 28 is mounted within one of the three compartments of the housing for alarm 10 behind a series of openings 29 in the cover 15 of the alarm (FIG. 1). Another of the internal compartments of alarm 10 includes conventional battery mounting means, not shown in detail, for mounting a storage battery 31 in the housing behind an access door 32. An alarm circuit, described below in conjunction with FIG. 4, is mounted in the horn compartment of the housing of alarm 10 on a circuit board 33 (FIG. 1); the alarm circuit includes an externally accessible test and reset switch 34 and a connector 35 for a remote alarm, both located in a recess 36 in cover 15.

An auxiliary sensor pad 37, essentially similar to the floor sensor pads 21, is stored within the third internal compartment of the housing of alarm 10 behind another access door 38 (FIG. 1). Pad 37 carries a pair of sensor electrodes 43 and 44, essentially the same as sensor electrodes 23 and 24. Electrodes 43 and 44 are connected to an elongated extension cord 45. The auxiliary sensor pad 37 is utilized for simultaneous monitoring of floor moisture conditions and of the water level in a sump or in a standpipe, as described in connection with FIGS. 4–6.

The alarm circuit 50 for alarm 10, FIG. 4, comprises a solid state switching device 51, in this instance a signal-controlled rectifier. The cathode of SCR 51 is connected to the negative terminal of battery 31. The anode of the SCR is connected to one terminal of horn 28 and the other operating terminal of the horn is returned to the positive terminal of battery 31 so that the main anode-cathode discharge path of switching device 51 is connected in series with the battery and the horn. A holding current resistor 52 and connector 35 are connected in parallel with horn 28.

The gate electrode of switching device 51 is electrically connected to each of the sensor electrodes 23 and to sensor electrode 43. The other sensor electrode in each pair, constituting the three electrodes 24, and the auxiliary sensor electrode 44, are all connected to the positive terminal of battery 31 through a current limiting resistor 54. A sensitivity-determining resistance 55 is connected between the gate electrode and the cathode of SCR 51. The test and reset switch 34 is connected in parallel with the main anode-cathode discharge path of SCR 51.

The floor moisture monitoring operaton of alarm 10, in the normal position of use illustrated in FIG. 2, is quite simple. As long as floor 26 is dry, the impedance between the sensor electrodes in each pair 23,24 is very high, amounting to an open circuit. Under these conditions, there is no complete electrical circuit between the positive and negative terminals of battery 31 (FIG. 4) and horn 28 is not actuated. Indeed, there is virtually no drain on the battery apart from very minor leakage currents. Switching device 51 remains non-conductive.

Whenever water accumulates on floor 26 beneath any of the feet 19, to a level sufficient to wet the sensor pad 21 in that foot, the resistance between the sensor electrodes 23,24 on that pad goes to a much lower value. With a sufficient accumulation of water to wet any of the sensor electrode pairs 23,24, a gating signal is supplied to the gate electrode of SCR 51 through the circuit from the positive terminal of battery 31 through resistor 54 and the affected sensor electrode pair, with an amplitude sufficient to render SCR 51 conductive. With SCR 51 conductive, an operating circuit is completed for horn 28 and the horn sounds to signify the occurrence of a dangerous condition of water accumulation on floor 26.

Horn 28 remains continuously energized until it is reset. This is readily accomplished by simply lifting alarm 10 from the floor (alarm 10 is quite small and light in weight), wiping the sensor electrodes 23 and 24 dry, and momentarily closing the test and reset switch 34. With switch 34 closed, SCR 51 is shunted. At the same time, the gate signal to the SCR is interrupted because the sensing electrodes have been wiped dry and again present a very high resistance in the gate electrode circuit. Accordingly, when switch 34 is again opened, alarm 10 is reset.

When a weather forecast indicates an impending storm that may create a water problem on floor 26, a test of alarm 10 is very much in order, to make certain that horn 28 is working and that battery 31 provides adequate power for the horn. An effective test is readily carried out simply by closing switch 34. With switch 34 closed, an operating circuit is established for horn 28. If the horn does not sound, the user has an opportunity to replace battery 31 and to check horn 28 to make sure that the alarm will serve its intended purpose. If an additional check is desired, alarm 10 can also be tested by thoroughly wetting any of the pairs of sensor electrodes 23 and 24.

FIG. 5 illustrates the manner in which alarm 10 is employed when the monitored floor 26 is a basement floor with a standpipe 61 projecting above the floor. The central opening 12 in alarm 10 (FIGS. 1 and 3) is large enough to permit alarm 10 to fit over a standpipe 61 of substantial size. Door 38 in the cover 15 of the housing of alarm 10 is opened and the auxiliary sensor pad 37 and cord 45 are pulled out of their storage position in the alarm housing. Cord 45 is long enough (preferably about eight feet) so that sensor pad 37 may be suspended within standpipe 16 at a level such that the alarm can respond to any dangerous rise of water within the standpipe. Of course, the level at which pad 37 is suspended within standpipe 61 can be adjusted to meet the requirements of the individual situation.

FIG. 6 illustrates the use of alarm 10 for simultaneous monitoring of moisture conditions on the floor 26 and of the level of water within a sump 71. As before, alarm 10 rests directly on floor 26. The auxiliary sensor pad 37 and cord 45 are pulled out of the alarm housing and the auxiliary sensor pad is suspended in sump 71. As in the standpipe arrangement of FIG. 5, the level of suspension for sensor pad 37 determines when the alarm will be sounded by a rising level of water in sump 71.

FIG. 7 shows the operating circuit for a remote alarm 80 that may be used in conjunction with alarm 10. The remote alarm 80 comprises a two terminal connector 35A that mates with the connector 35 in alarm 10

(FIGS. 1 and 4). One terminal 81 of connector 35A is connected, by a line 91, to the emitter of a transistor 82 and to the positive terminal of a battery 83. Conductor 91 is also connected to the base of transistor 82 by a load resistor 84. The other connector terminal 85 is connected, by a conductor 95, through a series resistor 86 to the base of transistor 82. The collector of transistor 82 is connected to one terminal of a horn or other alarm device 87, with the other terminal of horn 88 connected to the negative terminal of battery 83.

Connector 35A and the conductors 91 and 95 comprise a long two-wire cable that permits mounting of remote alarm 80 at a substantial distance from alarm 10. The other components of alarm 80 are mounted in a suitable housing (not shown).

The operation of remote alarm 80, when employed in conjunction with alarm 10, is quite simple. Whenever horn 28 (FIG. 4) is energized, as described above, transistor 82 (FIG. 7) is driven conductive in response to the resulting voltage across horn 28. This completes an operating circuit for remote horn 87, the remote horn being energized from its own battery 83 to avoid excessive drain on the battery 31 in the main alarm 10. When alarm 10 is reset, transistor 82 reverts to its normal non-conductive condition and the remote alarm is silenced. Remote alarm 80 may be positioned in an upstairs bedroom, for example, to give warning of flood conditions in a basement. Of course, testing of alarm 10 also serves to test remote alarm 80.

From the foregoing description it will be apparent that alarm 10 is quite simple and economical in construction. Only one switching device, the SCR 51, is employed, together with three resistors 52, 54, and 55. Resistor 55, which could be a potentiometer, sets the sensitivity of the alarm circuit 50 so that alarm 10 will not give a false warning under ordinary conditions of minor moisture condensation without actual accumulation of water on the floor surface. The annular shape of the housing of alarm 10 is of substantial advantage when the alarm is used in conjunction with a standpipe, as shown in FIG. 5. The cord-connected auxiliary sensor pad 37, with its sensor electrodes 43 and 44, makes the device readily adaptable for dual operation in conjunction with either a standpipe or a sump. The single switch 34 serves the dual purpose of resetting the alarm after a warning has been given and testing the alarm when conditions indicate that it might be brought into use.

We claim:

1. A self-contained water alarm for monitoring floor moisture comprising:

a housing having a plurality of support feet for supporting the housing on a floor with the bottom of the housing in close spaced relation to the floor;

a plurality of pairs of printed circuit sensor electrodes, each electrode pair being mounted on the outside of the bottom of the housing in a position protected from floor contact by the support feet, the sensor electrodes of each pair being in closely spaced relation to each other immediately above the floor on which the housing is supported, the resistance between the sensor electrodes being very high when the floor is dry and much lower when the floor is covered with water to a depth sufficient to contact the electrodes;

an electrically actuated audible alarm device, mounted within the housing;

battery mounting means for mounting a battery within the housing;

and an alarm circuit, mounted within the housing and interconnecting the alarm device, the battery, and the sensor electrodes, the alarm circuit comprising:

a solid-state switching device, connected to each pair of sensor electrodes and actuatable from a normal non-conductive condition to a sustained conductive condition in response to a low resistance condition between any pair of the sensor electrodes, the switching device having a main discharge path connected in series with the alarm device and the battery;

and an auxiliary pair of sensor electrodes mounted on a small pad and electrically connected in parallel with the housing-mounted pairs of sensor electrodes through an elongated extension cord to permit simultaneous monitoring of floor moisture and of the water level in a sump or in a standpipe, the housing including a storage compartment for storing the auxiliary electrode pad and cord when not in use.

2. A self-contained water alarm according to claim 1 in which the housing is of annular configuration, with a central aperture of substantial diameter enabling the alarm to slide downwardly over a standpipe to rest on a floor at the base of the standpipe.

3. A self-contained water alarm according to claim 2 and further comprising means for connecting a remote alarm to the alarm circuit,
the remote alarm including a second battery, a second alarm device, and a second switching device for connecting the second alarm device to the second battery for actuation whenever the main switching device is conductive.

4. A self-contained water alarm according to claim 2 in which each support foot includes a rim of closed configuration encompassing and protecting one sensor electrode pair but allowing access of water thereto.

* * * * *